United States Patent [19]

Nagatsu et al.

[11] 4,147,692
[45] Apr. 3, 1979

[54] NOVEL DIPEPTIDE DERIVATIVES, AND METHOD OF MEASURING ENZYMATIC ACTIVITY

[75] Inventors: Toshiharu Nagatsu, Yokohama; Shumpei Sakakibara, Suita, both of Japan

[73] Assignee: Ajinomoto Co., Inc., Tokyo, Japan

[21] Appl. No.: 878,826

[22] Filed: Feb. 17, 1978

[30] Foreign Application Priority Data

Feb. 26, 1977 [JP] Japan ................................. 52-20663
Jun. 16, 1977 [JP] Japan ................................. 52-71469

[51] Int. Cl.$^2$ ............................................ C07C 103/52
[52] U.S. Cl. ..................... 260/112.5 R; 195/103.5 R; 195/103.5 V

[58] Field of Search ................................. 260/112.5 R

[56] References Cited

U.S. PATENT DOCUMENTS

| 3,886,136 | 5/1975 | Claeson et al. ................ 260/112.5 R |
| 4,018,884 | 4/1977 | Cleeland, Jr. et al. ........ 260/112.5 R |

*Primary Examiner*—Delbert R. Phillips
*Attorney, Agent, or Firm*—Cooper, Dunham, Clark, Griffin & Moran

[57] ABSTRACT

The compound 7-glycylprolylamino-4-methylcoumarin and certain of its derivatives are utilized for the diagnosis of pathological conditions such as hepatic diseases and gastric cancer by measuring the enzymatic activity of X-prolyl dipeptidyl-aminopeptidase.

5 Claims, No Drawings

NOVEL DIPEPTIDE DERIVATIVES, AND METHOD OF MEASURING ENZYMATIC ACTIVITY

The present invention relates to novel dipeptide derivatives. More particularly it relates to 7-glycyl-prolylamino-4-methylcoumarin and acid salts thereof, which are useful as fluorogenic substrates for determining enzymatic activities, and also to N-protected derivatives of 7-glycylprolylamino-4-methylcoumarin useful as synthetic intermediates leading to said substrates.

A method has now been discovered for the synthesis of 7-glycylprolylamino-4-methylcoumarin having the following formula:

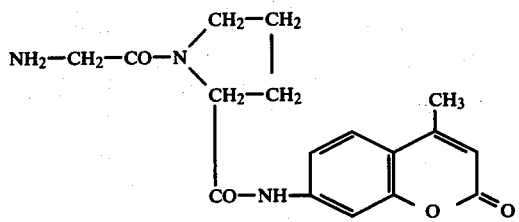

and acid salts thereof.

These compounds are useful as fluorogenic substrates for simple and highly sensitive determination of activity of enzymes such as X-prolyl dipeptidyl-aminopeptidase which was discovered previously in sera of various animals including humans and which decomposes X-L-proline p-nitroanilide into X-L-proline and p-nitroaniline (X being a neutral, acidic or basic amino acid residue). It is highly probable that this enzyme is identical with glycylprolyl β-naphthylamidase disclosed in Clin. Chim. Acta, 62 5-11 (1975).

Other novel compounds of the present invention are N-protected derivatives of 7-glycylprolylamino-4-methylcoumarin, which are useful intermediates leading to the novel substrates. Typical protecting groups for the amino radical of the glycine residue may include carbobenzoxy, t-butyloxycarbonyl, t-amyloxycarbonyl, trityl, p-nitrocarbobenzoxy, formyl, trifluoroacetyl, and phthaloyl radicals, all being used for synthesis of peptides, in addition to benzoyl, acetyl and tosyl radicals. Addition to and liberation from the amino radical may be achieved by an appropriate choice of the methods which have, for example, been used for protection of and liberation from the amino acids in synthesizing peptides.

The compounds of the present invention can be produced by a reaction of N-protected glycylproline with 7-amino-4-methylcoumarin (MCA). The N-protection can be achieved by an appropriate choice of the protecting group cited in the preceding paragraph. The synthetic reaction includes condensation by the use of such a reagent as dicyclohyxylcarbodiimide (DCC), N-ethyl-N-3-dimethylamino propylcarbodiimide, or a chloroformate ester such as isobutyl chloroformate under the existence of an organic base such as trimethyl-, triethyl- or a higher alkylamine or pyridine. For the condensation reaction, one may use a solvent such as dimethylformamide (DMF), chloroform, dichloromethane, ethylacetate ester, or an inert solvent such as dioxane or tetrahydrofuran (THF). Liberation of the protecting group from the condensation product may be achieved by an appropriate choice of the liberating methods conventional in synthesizing peptides. Catalytic hydrogenation may be one of them.

A specifically effective method is to use t-butyloxycarbonyl (BOC) radical for protection of the amino radical of the glycine residue and, subsequently, to use p-toluenesulfonic acid (TosOH) for elimination of the BOC radical from the N-protected derivative of 7-glycylprolylamino-4-methylcoumarin. This method, compared to others such as treatment with trifluoroacetic acid or hydrogen chloride in an organic solvent such as ethyl acetate, is advantageous because of (1) a small amount of the reagent (p-toluenesulfonic acid) required, (2) a small amount of by-product lowering the enzymatic accessibility of the substrate is produced, (3) a high purity of the final product after liberation of the protecting group is possible, (4) the simplicity of in the reaction and the subsequent procedures, and (5) a high yield. These characteristic advantages permit the production of a high yield of pure, crystalline product simply by recrystallization of the crude product from a suitable solvent such as a binary mixture of methanol and ethanol.

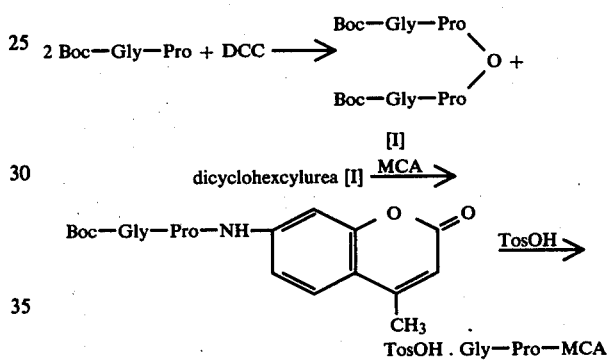

To produce either L- or D-proline-composed compound, one may use an optically active glycylproline as the starting substance or may apply ordinary methods of optical resolution to the final DL-mixture.

Enzymatic activity of X-prolyl dipeptidyl-aminopeptidase can be measured by assaying the amount of 7-amino-4-methylcoumarin formed by the enzymatic hydrolysis of 7-glycyl-L-prolylamino-4-methylcoumarin in an aqueous medium. The rate of the enzymatic hydrolysis reaction is proportional to the amount of enzyme present. Thus, the enzymatic activity can be determined by measuring the fluorescence intensity due to the formed 7-amino-4-methylcoumarin at 460nm with excitation at 380nm. This has been made possible by observation of the fact that the fluorescence intensity of 7-amino-4-methylcoumarin is 30 times as high as that of 7-glycyl-L-prolylamino-4-methylcoumarin.

It has been discovered in accordance with this that exo- and/or endocrinological fluids such as serum, cerebrospinal fluid, saliva and urine contain X-prolyl dipeptidylaminopeptidase which hydrolyses 7-glycyl-L-prolylamino-4-methylcoumarin into glycyl-L-proline and 7-amino-4-methylcoumarin, that the enzymatic activity is enormously high in the body fluid, especially in serum, of patient afflicted with a disease of the liver, kidney or its adjoining organs (for example, acute or chronic hepatitis, liver cirrhosis, and hepatic cancers), while the enzymatic activities in normal human sera are almost the same although there is slight but significant difference between males and females, especially between young males and females, that the enzymatic activity is extremely low in the fluid, especially in serum, of patient with solid cancer (gastric or pancreatic) and blood cancer (lymphocytic, neoplasms) and, accordingly, that the present method of the enzymatic activity measurement is useful in the diagnosis of various kinds of diseases, especially of hepatic and malignant diseases. Particularly, it is useful in diagnosing whether a gastric cancer has been metastasizing to the liver.

According to the process of this invention, it is possible to measure the enzymatic activity of X-prolyl dipeptidyl-aminopeptidase safely utilizing 7-glycyl-L-prolylamino-4-methylcoumarin or acid salts thereof and to do so without substantial possibility of carcinogenicity and with high reliability and reproducibility.

7-glycyl-L-prolylamino-4-methylcoumarin can be used as the substrate either in the free amino form or in the salt form with an organic acid such as p-toluenesulfonic acid or with an inorganic acid such as hydrochloric or hydrobromic acid, none of them inhibiting the enzymatic reaction. These salts may be easily obtained by contacting the free compound with an acid in a suitable solvent.

The enzymatic activity can be measured without difficulties: 7-glycyl-L-propylamino-4-methylcoumarin or acid salts thereof is dissolved to an optimum concentration in water or, to enhance dissolution, in an aqueous solution of surfactant. The optimum pH of the substrate solution is adjusted experimentally considering the rates of enzymatic hydrolysis and non-enzymatic decomposition. The optimum pH is usually in the range of 6 to 9.

To measure the enzymatic activity, the enzyme (sample solution) is reacted at 30°–45° C. with a substrate in its solution for a given time and, after the ordinary procedures for enzyme deactivation, the amount of 7-amino-4-methylcoumarin formed in the reaction mixture is determined by the method described in the preceding paragraph.

The present invention is explained precisely in the following Examples:

EXAMPLE 1

A portion (585mg=5m mole) of isobutyl chloroformate was added at $-5\sim-10°$ C. to a THF solution (30ml) of N-carbobenzoxyglycyl-N-proline (1.53g=5m mole) and triethylamine (0.7ml=5m mole) and, after stirring for 10 minutes, a DMF solution (20ml) of 7-amino-4-methylcoumarin (875mg = 5m mole) was added to the reaction mixture. The entire portion was stirred for 30 minutes at $-5\sim-10°$ C. and subsequently, for 4 hours at room temperature. After distilling-off the solvent in vacuo, the residue was treated with ethyl acetate (75ml) and the extracting ester was washed successively with 1 N hydrochloric acid, water, aqueous 5% sodium bicarbonate and water and dried with anhydrous sodium sulfate. The crude product obtained by vacuum distillation of the ester was purified by column chromatography using 50g of silica gel as adsorbent and ethyl acetate or its binary mixture with benzene (2:1 in volume) as eluent and precipitated with a mixture of ethyl acetate (10ml) and n-hexane (30ml) to give 1.4g (yield, 60%) of 7-(N-carbobenzoxyglycyl-L-prolyl)-amino-4-methylcoumarin.

M. p., 107.5°–113.5° C.; $[\alpha]_D^{18}$, $-116.1°$ (C=1, in DMF).

The crystals gave a single spot ($R_f=0.65$) on the thin layer chromatogram with a ternary eluent of chloroform, methanol, and acetic acid in 95:5:3 volume ratio.

Elemental analysis: Found, C, 62.49%; H, 5.81%, N, 8.96%. Calcd. for $C_{25}H_{25}N_3O_6.H_2O$, C, 62.36%, H, 5.65%, N, 8.75%.

To a solution of 7-(N-carbobenzoxyglycyl-L-prolyl)-amino-4-methylcoumarin (464mg=1m mole) in a binary mixture of 80% acetic acid (10ml) and methanol (50ml), a portion (50mg) of 10% Pd-C was added for catalytic hydrogenation for 4 hours to yield 7-glycyl-L-prolylamino-4-methycoumarin. After filtering-off the catalyst, p-toluenesulfonic acid monohydrate (190mg=1m mole) was added to the filtrate for freeze-drying. A portion of water (50ml) was added to the residue, the resulting solution was freeze-dried again, and the colorless powder obtained (465mg) was reprecipitated from ethanol (10ml)/ ether (50ml) mixture to yield 400mg [77.4% for yield from 7-(N-carbobenzoxyglycyl-L-prolyl)-amino-4-methylcoumarin] of 7-glycyl-L-prolylamino-4-methylcoumarin p-toluenesulfonate.

M. p., 182.0°–188.5° C.; $[\alpha]_D^{20}$, $-111.0°$ (C=1, in acetic acid).

The crystals gave a single spot on any of the following thin layer chromatograms:

(1) $R_f=0.4$ for n-butanol/acetic acid/water (4:1:5 in volume ratio).

(2) $R_f=0.7$ for n-butanol/pyridine/acetic acid/water (15:10:3:12).

Elemental analysis: Found, C, 54.08%, H, 5.44%, N, 7.58%. Calcd. for $C_{24}H_{27}O_7N_3S.3/2H_2O$. C, 54.53%, H, 5.72%, N, 7.95%.

EXAMPLE 2

A portion (10.3g=0.05 mole) of dicyclohexylcarbodiimide (DCC) was added dropwise under stirring at 0° C. to a solution of N-Boc-glycyl-L-proline prepared in accordance with the method described in J. Chem. Soc. (C), 954 (1969) (27.2g=0.1 mole) in dried THF (100ml) and the reaction mixture was kept under continuous stirring for 45 minutes. To the filtrate obtained by filtering-off of dicyclohexyl urea precipitated in the mixture, was added at 0° C. a solution of 7-amino-4-methylcoumarin (8.75g=0.05 mole) in dimethylformamide (DMF) (60ml). After standing overnight at room temperature, the reaction mixture was concentrated in vacuo to give a residue which was dissolved in ethyl acetate (300ml.). The solution was washed successively with 1 N hydrochloric acid, aqueous 5% sodium bicarbonate and water, dried with anhydrous magnesium sulfate, and concentrated in vacuo. The residue was recrystallized from a binary mixture of ethyl acetate (150ml) and n-hexance (70ml) to give 20.1g (yield, 93.4%) of crystalline 7-(n-BOC-glycyl-L-prolyl)-amino-4-methylcoumarin.

M. p., 125.0°–128.5° C.; $[\alpha]_D^{20}$, $-123.0°$ (C=1, in DMF).

Elemental analysis: Found, C, 61.74%, H, 6.44%, N, 9.76%. Calcd. for $C_{22}H_{27}O_6N_3$. C, 61.52%, H, 6.34%, N, 9.79%.

The BOC radical in the above compound was removed by the following method: A portion (5.7g=0.03 mole) of p-toluenesulfonic acid monohydrate was added under stirring to a solution of 7-(N-BOC-glycyl-L-prolyl)-amino-4-methylcoumarin (10.8g=0.025 mole) in acetic acid (20ml) and the reaction mixture was kept standing for 90 minutes at room temperature. An excess amount of dried ether was added to the mixture for crystallizing all of the reaction products, which were subsequently filtered, washed with ether, and recrystallized twice from a binary mixture of methanol (30ml) and ether (300ml) to yield 10.5g (yield, 84%) of 7-glycyl-L-prolylamino-4-methylcoumarin p-toluenesulfonate in crystalline form.

M. p., 183.5°–189.5° C.; $[\alpha]_D^{20}$, $-112.5°$ (C=1, in acetic acid).

Elemental analysis: Found, C, 56.18%, H, 5.69%, N, 8.18%. Calcd. for $C_{24}H_{27}O_7N_3S \cdot \frac{1}{2}H_2O$. C, 56.45%, H, 5.53%, N, 8.23%.

EXAMPLE 3

By the use of 7-glycyl-L-prolylamino-4-methylcoumarin p-toluenesulfonate (Gly-Pro-MCA Tosylate) for a substrate (2m mole concentration) and purified X-prolyl dipeptidyl-aminopeptidase from human submaxillary gland for the enzyme, experiments were made under the conditions listed below.

| Mixing solution | Experiment (E) | Control (C) | Standard (S) | Blank (B) |
| --- | --- | --- | --- | --- |
| 0.15 M Glycine/NaOH buffer (pH = 8.7), μl | 40 | 40 | 40 | 40 |
| 2 mM Gly-Pro-MCA Tosylate, μl | 25 | 25 | 25 | 25 |
| Enzyme solution, μl | 0–35 | — | — | — |
| Water, μl | 35–0 | 35–0 | 5 | 35 |
| 10 μM MCA | — | — | 30 | — |
| Incubation at 37° C for 30 minutes | | | | |
| 1 M sodium acetate buffer (pH = 4.2), μl | 1.0 | 1.0 | 1.0 | 1.0 |
| Enzyme solution, μl | — | 0–35 | — | — |

The amount of 7-amino-4-methylcoumarin (MCA) formed by the enzymatic reaction for a varied reaction (incubation) time was determined by the fluorescence analysis. The following table indicates the time dependence of the MCA amount calculated by $$\frac{E - C}{S - B} \times 0.3 \text{n mol}$$

| Reaction (incubation) time (min.) | MCA formed (n mole) |
| --- | --- |
| 15 | 1.35 |
| 30 | 2.80 |
| 60 | 5.40 |
| 90 | 8.00 |
| 120 | 10.60 | where E, C, S, and B are the fluorescence intensify measured at 460 nm with excitation at 380nm. It is obvious that the MCA amount is proportional to the reaction (incubation) time.

The following table gives the effect of the enzyme amount upon the amount of MCA formed by the reaction at 37° C. for 30 minutes. It is evident that the MCA amount is proportional to the amount of the enzyme.

| Amount of enzyme (pg) | MCA formed (p mole) |
| --- | --- |
| 143 | 25.7 |
| 1430 | 262.6 |
| 4290 | 773 |
| 14300 | 272.2 |

An appropriate use of the substrate enables to determine the enzymatic activity by comparing the amount of MCA thereby formed with that on the calibration curve and, accordingly, to apply to diagnosing the diseases cited hereinbefore.

EXAMPLE 4

The following table shows the enzymatic activities of cerebrospinal fluid, serum, saliva and urine from normal humans, which were measured in the manner similar to that of EXAMPLE 3.

| Enzyme solution | Number of subjects | Enzyme activity (av. ± S. E.) | |
| --- | --- | --- | --- |
| | | n mole/min./ml | n mol/min./mg. protein |
| cerebrospinal fluid | 17 | 0.0773 ± 0.0131 | 0.399 ± 0.036 |
| serum | 5 | 38.2 ± 2.2 | 0.510 ± 0.036 |
| saliva | 5 | 10.51 ± 1.79 | 8.91 ± 3.70 |
| urine | 19 | 1.46 ± 0.31 | 1.69 ± 0.31* |

*n mol/min./mg. creatinine

An appropriate use of the present compounds as the substrate permits a determination of the enzymatic activity of X-prolyl dipeptidyl-aminopeptidase in serum in a volume less than 1 μl, to assist in the diagnosis of hepatic diseases and gastric cancer. Also, the method using the present compounds permits determination of the enzymatic activity in cerebrospinal fluid, saliva and urine.

What is claimed is:

1. 7-Glycyl-prolylamino-4-methylcoumarin, and acid salts and N-endo-protected derivatives thereof.
2. The compounds of claim 1, wherein the stereochemical configuration of the proline residue is the L-form.
3. 7-Glycyl-L-prolylamino-4-methylcoumarin.
4. 7-Glycyl-L-prolylamino-4-methylcoumarin p-toluenesulfonate.
5. 7-glycyl-prolylamino-4-methylcoumarin or acid salts thereof.

* * * * *